United States Patent [19]

Hayes

[11] Patent Number: 5,161,404
[45] Date of Patent: Nov. 10, 1992

[54] ROD BENDER

[75] Inventor: S. Kyle Hayes, Warsaw, Ind.

[73] Assignee: Zimmer, Inc., Warsaw, Ind.

[21] Appl. No.: 780,593

[22] Filed: Oct. 23, 1991

[51] Int. Cl.$^5$ .............................................. B21D 7/00
[52] U.S. Cl. .................................... 72/458; 140/106; 72/479
[58] Field of Search .................. 72/458, 459, 479; 140/106

[56] References Cited

U.S. PATENT DOCUMENTS

| | | |
|---|---|---|
| 124,362 | 3/1872 | Kernon . |
| 811,516 | 1/1906 | Mull . |
| 951,717 | 3/1910 | Andres ................................ 72/381 |
| 1,042,112 | 10/1912 | Hartman . |
| 1,326,907 | 1/1920 | Bond .................................... 72/458 |
| 1,479,762 | 1/1924 | Wagenbach . |
| 2,087,125 | 7/1937 | Smith et al. ....................... 140/106 |
| 2,502,713 | 4/1950 | Fagge ................................. 153/45 |
| 3,459,030 | 8/1969 | Wilson ................................ 72/458 |
| 3,610,019 | 10/1971 | Denninger ......................... 72/386 |
| 3,709,264 | 1/1973 | Amman ............................. 140/106 |
| 3,824,834 | 7/1974 | Durham ............................ 72/387 |
| 3,901,064 | 8/1975 | Jacobson ........................... 72/388 |
| 4,034,595 | 7/1977 | Smith ................................. 72/458 |
| 4,091,845 | 5/1978 | Johnson ............................. 140/106 |
| 4,132,100 | 1/1979 | Schuler ............................... 72/217 |
| 4,304,117 | 12/1981 | Rawson ............................. 72/388 |
| 4,474,046 | 10/1984 | Cook .................................. 72/409 |
| 4,691,555 | 9/1987 | Vaughan ............................ 72/459 |
| 4,716,757 | 1/1988 | McGregor et al. ............... 72/458 |

FOREIGN PATENT DOCUMENTS

| | | |
|---|---|---|
| 0010650 | 3/1908 | Denmark ............................ 72/458 |
| 0177266 | 11/1907 | Fed. Rep. of Germany . |
| 0479753 | 7/1929 | Fed. Rep. of Germany ........ 72/458 |
| 511864 | 1/1921 | France . |
| 0240505 | 7/1946 | Switzerland ....................... 72/458 |
| 15345 | of 1911 | United Kingdom . |
| 126994 | 5/1919 | United Kingdom . |

OTHER PUBLICATIONS

Zimmer, Inc.—1987 catalog p. B66 (prod. No. 5402-01); B70 (prod. No. 811); B71 (prod. Nos. 805-01/03 and 693); C59 (prod. Nos. 2371-01 and 2371-02); C60 (prod. Nos. 2371-30 and 2440); C61 (prod. No. 1179-20).

Zimmer, Inc.—Lit. No. 81-040-0000-0966-"Buttress Plating" and Plate Contouring—page from ECT Fracture Fixation Reference Manual—1981.

Zimmer, Inc.—Lit. No. 83-040-1179-0177—"New Pelvic Plates for Internal Fixation of Acetabular and Pelvic Fracture"—1983.

Primary Examiner—David Jones
Attorney, Agent, or Firm—Margaret L. Geringer

[57] ABSTRACT

An instrument for bending a rod, wherein the instrument includes an elongated handle and an angled tip extending therefrom. The tip includes a channel or bore therethrough for receiving the rod. The top side of the tip may include a flat surface thereon. Two such instruments are used to bend a rod by inserting one end of the rod into the channel of one instrument and the other end of the rod into the channel of the other instrument. Force is applied to the instruments to preliminarily bend the rod. The instruments are each then rotated 180 degrees, and further force is then applied to the instruments to further bend the rod. The force may be applied until the flat surface on each instrument abuts each other.

7 Claims, 3 Drawing Sheets

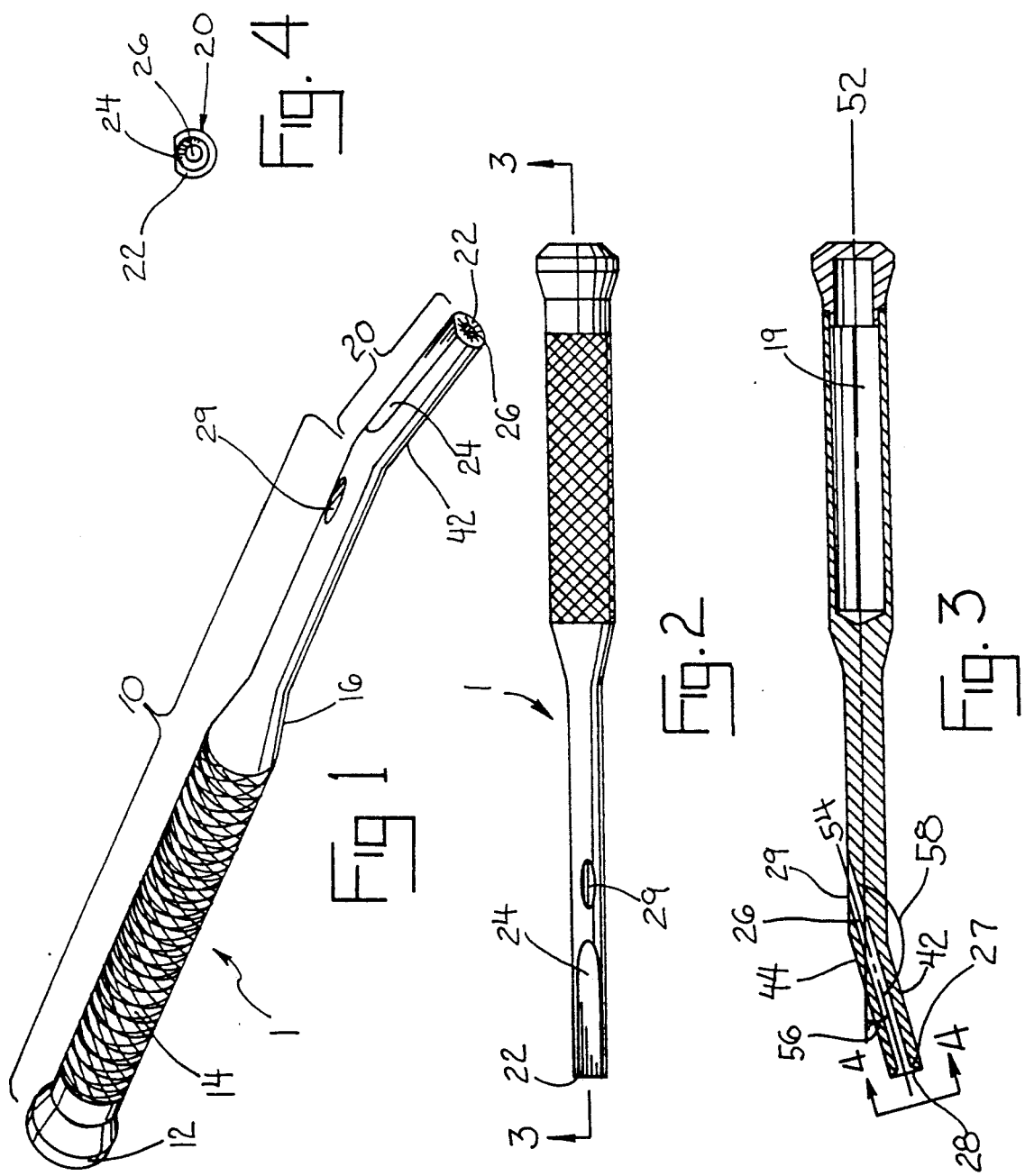

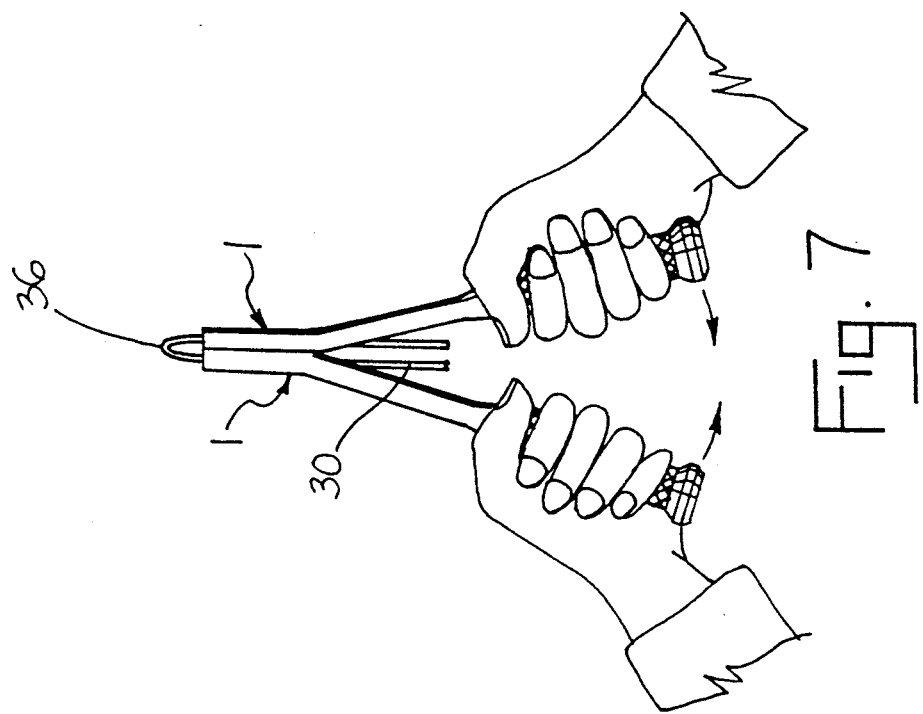
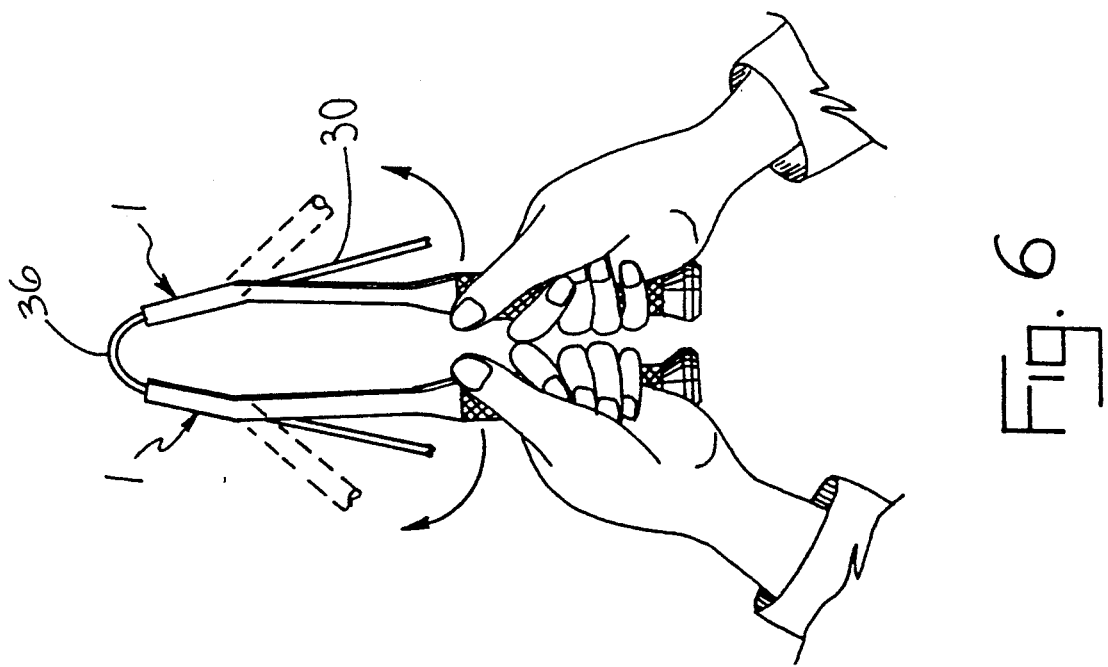

ROD BENDER

BACKGROUND OF THE INVENTION

The present invention generally relates to instruments for bending rods.

A wide variety of instruments are known in the art for bending rods. Some bending instruments utilize a three-post bending combination in association with a handle or lever combination. In such a device, the center post is generally located at the pivot of the two-arm device and each of the two outer posts are mounted on an arm so as to be pivotable therewith about the center post. Application of manually applied force to the handles or lever mechanism generally causes the outer posts to orbit about the center post in such a manner as to bend a rod-like article positioned between the center post and the outer posts about the center posts. An example of a bending tool utilizing a three-post bending combination is described in U.S. Pat. No. 4,474,046 to Cook. Another is described in U.S. Pat. No. 4,304,117 to Rawson. This type of bending tool utilizes leverage against a post-member in order to help effect the bending.

Another style of device utilizes two Bending Tubes, such as product number 1292-98 sold by Zimmer, Inc. in Warsaw, Ind. These 1292-98 Bending Tubes are tubular, straight rods with an interior channel in each. One end of a straight rod is placed in one channel of one instrument and the other end of the rod is placed in the channel of the other instrument. An external key or lever may be threaded through a hole in the wall of each instrument to press against the rod in the channel to secure the rod's position in the channel and prevent it from sliding within the channel. Manual pressure is then applied to the handles of both instruments to swing the handle ends toward each other and thus bend the rod. However, with the two straight instruments it is difficult to initiate the bend or get the bend in the rod started.

OBJECTS OF THE INVENTION

A principal object of this invention is to provide a rod bending tool of the type having a channel or bore in the distal end for accepting a rod or other such elongated item to be bent, such that the tool incorporates an angled tip to enable the user of the tool to initiate the bend in the rod more easily than with a straight tool.

Another object of the invention is to provide two rod benders which can each be rotated about the axis of each instrument's respective angled tip after the bend in the rod has been started, such that the rod can then be more conveniently bent to a greater degree after such rotation than if the instruments had not been rotated.

A further object of the invention is to provide a flat surface on the top surface of the angled tip of the rod bender, such that after the two rod benders are each rotated, the rod can be bent until the flat surface on one tool meets with the flat surface on the other tool. The flat surface helps prevent the tools from turning or slipping on one another and cracking the user's knuckles together.

SUMMARY OF THE INVENTION

The present invention accomplishes all of the above objects of invention. The present invention provides a rod bending instrument which includes an elongated handle and an angled tip extending therefrom. The tip includes a channel or bore therethrough for receiving the rod. The top side of the tip may include a flat surface thereon. Two such instruments are used to bend a rod by inserting one end of the rod into the channel of one instrument and the other end of the rod into the channel of the other instrument. Force is applied to the instruments to preliminarily bend the rod. The instruments are each then rotated 180 degrees, and further force is then applied to the instruments to further bend the rod. Force may be applied until the flat surface on each instrument abuts each other.

BRIEF DESCRIPTION OF THE DRAWINGS

These features and objects of the invention, as well as others will become apparent to those skilled in the art by referring to the accompanying drawings in which:

FIG. 1 is a perspective view of the rod bender of the present invention;

FIG. 2 is a top plan view of the rod bender of FIG. 1;

FIG. 3 is a cross-sectional view taken along lines 3—3 of FIG. 2;

FIG. 4 is an end view taken along lines 4—4 of FIG. 3;

FIG. 6 is a side view of the two rod benders of FIG. 5 shown after manual force has been applied to the two rod benders to bend the rod, with the arrows representing the direction that the rod benders are each to be rotated about the respective angled tip axis, with the rotated position shown in partial phantom lines; and FIG. 7 is a side view of the two rod benders of FIG. 6 shown in the rotated position, with the arrows representing the general direction of force that was applied to the two rod benders to bring them to this final position.

DETAILED DESCRIPTION OF THE INVENTION

Figure 5:
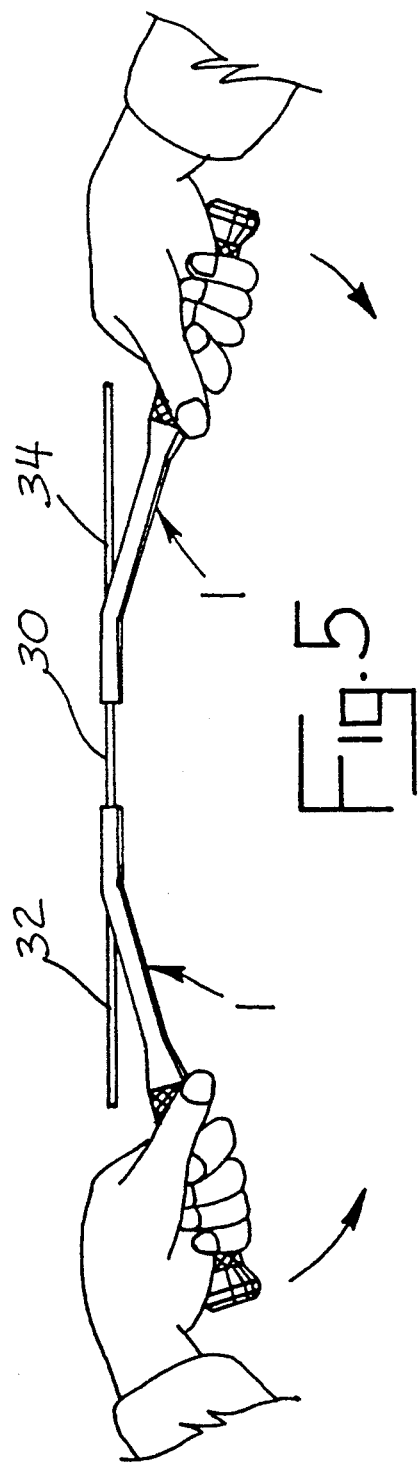
FIG. 5 is a side view of two rod benders positioned on a straight rod, with the downward arrows showing the general direction of force that is to be applied to the two rod benders.

The preferred embodiment disclosed herein is not intended to be exhaustive o to limit the invention to the precise form disclosed. Rather, this embodiment is described to enable others skilled in the art to utilize its teachings.

FIGS. 1-7 illustrate a particularly advantageous embodiment of the rod bender according to this invention. It is noted that the rod bender of this invention is particularly suitable for use in bending spinal rods for spinal surgery; however, such use is not limited thereto.

The rod bender 1 includes an elongated handle 10 having a first axis 52 and an angled tip 20 extending downwardly therefrom and having a second axis 54. The first and second axes 52 and 54 form an obtuse angle 58 therebetween in the downward direction, and an acute angle 56 therebetween in the upward direction. The angled tip 20 includes a channel or bore 26 therethrough for receiving a rod 30. The channel 26 is drilled or formed along the second axis 54 of angled tip 20. (It is noted that the terms downward and upward are merely relative for the sake of reference.)

The tip 20 has a topside 44 in the upward direction and a bottom side 42 in the downward direction. The top side 44 includes a flat surface 24 thereon.

The tip 20 includes distal face 22. The channel 26 extends throughout the angled tip 20 forming a first opening 28 through the distal face 22 at one end of the channel 26, and forming a second opening 29 through the instrument at the other of the channel 26.

The acute angle 56 of the angled tip is preferably in the range of about 10 to 30 degrees, with the preferred acute angle 56 being about 15 degrees. This acute angle in the instrument allows the user of the instrument 1 to initiate the bend in the rod 30 more easily, than if the rod bender instrument was straight. The angled rod bender instrument gives more leverage to the user than the prior art straight rod bending device. Thus, the angled instrument 1 takes less force to initiate the bend in the rod.

The elongated handle portion 10 of rod bender instrument 1 may suitably be about 10 to 11 inches long, with the angled tip 20 being about 1½ to 2 inches long. The handle 10 includes a proximal end knob 12 which may be formed as a separate piece as shown in FIG. 3, and press-fit and welded into hollow chamber 19 of the handle 10. Alternatively, the knob 12 may be integrally formed with the rest of the instrument 1. The knob 12 may be enlarged relative to the adjacent portion of the handle 10 to help prevent the instrument 1 from slipping out of the user's hands. The portion of the handle 10 located toward the knob 12 may include knurling 14 for gripping purposes. This knurled portion may have a circular cross-section of about one inch in diameter. The handle 10 then may taper down at 16 to a smaller diameter of about a half an inch in diameter for the remainder of the instrument 1 (preferably about 0.56 inch). The channel 26 may be about 0.196 to 0.2 inches in diameter to allow the rod (such as a 3/16 inch or 0.1875 inch diameter rod) to pass freely through the channel 26. The channel 26 may include a radiused portion 27 leading from the channel 26 to first opening 28 at distal face 22 to help eliminate any sharp edges that might cause any marring or damage of the rod finish during bending. These suggested dimensions are not intended to be limiting, but rather are indicative of suitable dimensions. Further, it is noted that the rod bender instrument 1 may be adapted to accommodate other diameter elongated rods 30 or other similar elongated devices to be bent. For example, the rod bender 1 could be dimensioned to accommodate a ¼ inch rod or other suitable diameter rods for bending. Also rod bender 1 may be utilized to bend rods of varying length, for example lengths ranging up to 20 or more inches long.

The instrument 1 may be made out of stainless steel or any other suitable material, and may be made by any suitable manufacturing method.

With the embodiment of FIGS. 1-7, the rod 30 is inserted from a free end of the rod through first opening 28 of channel 26, and then the instrument 1 slid along the rod to the desired position, or for removal, rod bender 1 is slid all the way back off of a free end of rod 30 to remove rod bender 1 from rod 30.

The FIGS. 5-7 illustrate the method of using two rod benders 1. In FIG. 5, the first end 32 of rod 30 is inserted into channel 26 of one of the rod bender instruments 1, and the second end 34 of rod 30 is inserted into the channel 26 of the other instrument 1. Thus, the second axis 54 of the angled tip 20 of each instrument 1 is aligned with the axis of elongated rod 30. A suitable length of rod 30 is left extending between the distal faces 22 of each rod bender 1, leaving enough length between to form the desired bend in the rod. The free ends of the rod extend out through the second opening 29 of each instrument 1, as shown in FIG. 5. The amount of rod extending from second opening 29 of each rod bender depends on the length of the rod 30 and the desired location for the bend in the rod. Force is then manually applied to each handle 10 to swing the two handles toward each other (such as shown by the arrows in FIG. 5), to create a bend 36 in the rod 30 as shown in FIG. 6. Both instruments 1 are then rotated about each instrument's second (tip) axis 54, and thus about rod 30. This rotation is shown by the arrows in FIG. 6 to illustrate the change of position of the instruments from the original position to the rotated position (shown partially in phantom lines in FIG. 6). This rotation, as shown, is substantially a 180 degree rotation about the second axis 54 of each instrument. After the two instruments are rotated to this rotated position, further force is manually applied to continue to swing the two handles toward each other, as shown by the arrows in FIG. 7, to further increase the bend 36 in the rod 30. This further force can be applied until the flat surface 24 of each rod bender instrument 1 abuts each other, as shown in FIG. 7. The flat surfaces 24 help keep the rod benders 1 from turning or slipping on one another and cracking the user's knuckles together (as might happen if this surface was rounded instead of flat).

The angled tip 20 enables the rod benders 1 to be rotated or turned back on each other, and the angle which initially aids in initiating the bend in the rod 30, now enables the rod to be more conveniently bent further than if the instrument was straight, because as shown in FIG. 7, the handles 10 of the rotated instruments now angle away from each other. This leaves room between the two instruments for the user's hands to continue to grip the handles 10, as the handles approach each other without pinching the user's hands. The two angled rod benders 1 enable a rod 30 to be conveniently bent to provide substantially a 180 degree bend in the rod, so that the two ends 32 and 34 are substantially parallel with bend 36 therebetween, forming substantially a "U" shape. The ability to conveniently achieve such a tight bend is very advantageous. However, it is noted that the orientation and/or degree of the bend may vary depending upon the situation and the type of bend desired. For example, if a less severe bend was desired, the user could stop applying force when the desired bend is achieved.

Further, it should be understood that the present invention is not to be limited to the precise forms disclosed, but may be modified in keeping with the appended claims.

I claim:

1. An instrument for bending a rod comprising an elongated handle having a first axis and an angled tip extending at an angle therefrom and having a second axis, such that the first and second axes form an obtuse angle therebetween in a first direction, and an acute angle therebetwen in a second direction opposite the first direction, and wherein the tip includes a channel therethrough for receiving the rod and wherein the tip has a length and includes a distal face and the channel is a cylindrical channel which extends throughout the length of the angled tip forming a first opening through the distal face at one end of the channel and forming a second opening through the instrument at the other end of the channel, and wherein the channel is radially enclosed between the first opening at the distal face of the angled tip and the second opening.

2. The instrument of claim 1 wherein the acute angle is in the range of about 10 to 30 degrees.

3. The instrument of claim 1 wherein the acute angle is about 15 degrees.

4. An instrument for bending a rod comprising an elongated handle having a first axis and an angled tip extending at an angle therefrom and having a second axis, such that the first and second axes form an obtuse angle therebetween in a first direction, and an acute angle therebetween in a second direction opposite the first direction, and wherein the tip includes a channel therethrough for receiving the rod and wherein the tip has a length and includes a distal face and the channel is a cylindrical channel which extends throughout the length of the angled tip forming a first opening through the distal face at one end of the channel and forming a second opening through the instrument at the other end of the channel, and wherein the channel is radially enclosed between the first opening at the distal face of the angled tip and the second opening, and wherein the tip has a first side in the second direction, and wherein the first side includes a flat surface thereon.

5. A method of bending a rod utilizing two instruments each having an elongated handle having a first axis and an angled tip extending therefrom and having a second axis, such that the first and second axes form an angle therebetween, and wherein the tip includes a channel therethrough for receiving the rod, and wherein the rod is an elongated rod having a first end and a second end, and wherein the method comprises the following steps:
 a) inserting the first end of the rod into the channel of one of the instruments;
 b) inserting the second end of the rod into the channel of the other instrument, and thus aligning the second axis of each instrument with the elongated rod;
 c) applying force to each handle to swing the two handles toward each other to create a bend in the rod;
 d) rotating each instrument about each instrument's second axis;
 e) subsequent to said rotating step, applying further force to each handle to continue to swing the two handles toward each other to further increase the bend in the rod.

6. The method of claim 5 wherein the rotating step comprises rotating each instrument 180 degrees about each instrument's second axis.

7. The method of claim 6 wherein the tip of each instrument has a top side and wherein the top side includes a flat surface thereon, and wherein the step of applying further force further includes the step of applying such further force until the flat surface of each instrument abuts each other.

* * * * *